United States Patent
Huddleston

(10) Patent No.: US 12,144,727 B2
(45) Date of Patent: Nov. 19, 2024

(54) TETHER ATTACHMENT FOR MITRAL VALVE

(71) Applicant: Tendyne Holdings, Inc., St. Paul, MN (US)

(72) Inventor: Preston James Huddleston, Maplewood, MN (US)

(73) Assignee: Tendyne Holdings, Inc, St. Paul, MN (US)

( * ) Notice: Subject to any disclaimer, the term of this patent is extended or adjusted under 35 U.S.C. 154(b) by 193 days.

(21) Appl. No.: 17/372,900

(22) Filed: Jul. 12, 2021

(65) Prior Publication Data
US 2022/0015899 A1    Jan. 20, 2022

Related U.S. Application Data
(60) Provisional application No. 63/052,160, filed on Jul. 15, 2020.

(51) Int. Cl.
*A61F 2/24*        (2006.01)
*A61B 17/04*       (2006.01)

(52) U.S. Cl.
CPC .......... *A61F 2/2418* (2013.01); *A61F 2/243* (2013.01); *A61F 2220/0008* (2013.01); *A61F 2220/0075* (2013.01)

(58) Field of Classification Search
None
See application file for complete search history.

(56) References Cited

U.S. PATENT DOCUMENTS

| | | | |
|---|---|---|---|
| 3,657,744 A | 4/1972 | Ersek | |
| 3,898,701 A * | 8/1975 | La Russa | A61F 2/2412 |
| | | | 137/846 |
| 4,275,469 A | 6/1981 | Gabbay | |
| 4,423,730 A | 1/1984 | Gabbay | |
| 4,491,986 A | 1/1985 | Gabbay | |

(Continued)

FOREIGN PATENT DOCUMENTS

| | | |
|---|---|---|
| DE | 19857887 A1 | 7/2000 |
| DE | 10121210 B4 | 11/2005 |

(Continued)

OTHER PUBLICATIONS

"Catheter-Implanted Prosthetic Heart Valves: Transluminal Catheter Implantation of a New Expandable Artificial Heart Valve in the Descending Thoracic Aorta In Isolated Vessels and Closed Chest Pigs", Knudsen et al., The International Journal of Artificial Organs, vol. 16, No. 5, May 1993, pp. 253-262.

(Continued)

*Primary Examiner* — Ann Schillinger
(74) *Attorney, Agent, or Firm* — SLEMAN & LUND LLP

(57) ABSTRACT

A prosthetic mitral valve with improved blood flow to the left ventricular outflow tract. The prosthetic mitral valve includes an expandable outer stent having an atrial end and a ventricular end, and an expandable inner stent attached to and at least partially positioned within the outer stent. The inner stent has an inflow end, an outflow end and a tether connector securing a tether. A valve assembly including a cuff and a plurality of leaflets may be disposed within the inner stent. The tether connector is positioned at the inflow end of the inner stent so as to shorten the overall length of the prosthetic valve.

11 Claims, 5 Drawing Sheets

(56) References Cited

U.S. PATENT DOCUMENTS

| | | | |
|---|---|---|---|
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,078,720 A | 1/1992 | Burton et al. | |
| 5,332,402 A * | 7/1994 | Teitelbaum | A61F 2/2424 623/2.35 |
| 5,411,552 A | 5/1995 | Andersen et al. | |
| 5,415,664 A | 5/1995 | Pinchuk | |
| 5,480,423 A | 1/1996 | Ravenscroft et al. | |
| 5,484,444 A | 1/1996 | Braunschweiler et al. | |
| 5,702,418 A | 12/1997 | Ravenscroft | |
| 5,824,041 A | 10/1998 | Lenker et al. | |
| 5,843,167 A | 12/1998 | Dwyer et al. | |
| 5,855,601 A | 1/1999 | Bessler et al. | |
| 5,924,424 A | 7/1999 | Stevens et al. | |
| 5,935,163 A | 8/1999 | Gabbay | |
| 5,961,549 A | 10/1999 | Nguyen et al. | |
| 5,968,068 A | 10/1999 | Dehdashtian et al. | |
| 5,980,533 A | 11/1999 | Holman | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,269,819 B1 | 8/2001 | Oz et al. | |
| 6,306,141 B1 | 10/2001 | Jervis | |
| 6,332,893 B1 * | 12/2001 | Mortier | A61F 2/2487 623/2.41 |
| 6,368,348 B1 | 4/2002 | Gabbay | |
| 6,391,050 B1 | 5/2002 | Broome | |
| 6,419,695 B1 | 7/2002 | Gabbay | |
| 6,458,153 B1 | 10/2002 | Bailey et al. | |
| 6,468,299 B2 | 10/2002 | Stack et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 * | 6/2003 | Gabbay | A61F 2/2409 623/2.38 |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,797,002 B2 * | 9/2004 | Spence | A61F 2/2454 623/2.38 |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 * | 6/2008 | Schreck | A61F 2/2433 623/2.18 |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,857,845 B2 | 12/2010 | Stacchino et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 8,252,051 B2 * | 8/2012 | Chau | A61F 2/2436 623/2.14 |
| D684,692 S | 6/2013 | Braido | |
| 8,628,571 B1 * | 1/2014 | Hacohen | A61F 2/2403 623/2.18 |
| 8,840,661 B2 | 9/2014 | Manasse | |
| 8,840,663 B2 | 9/2014 | Salahieh et al. | |
| 9,480,559 B2 * | 11/2016 | Vidlund | A61F 2/2418 |
| 9,827,092 B2 * | 11/2017 | Vidlund | A61F 2/2439 |
| 9,895,221 B2 * | 2/2018 | Vidlund | A61F 2/2439 |
| 10,201,419 B2 * | 2/2019 | Vidlund | A61B 17/0057 |
| 10,299,917 B2 * | 5/2019 | Morriss | A61F 2/2433 |
| 10,463,489 B2 * | 11/2019 | Christianson | A61F 2/2439 |
| 10,470,877 B2 * | 11/2019 | Tegels | A61F 2/2418 |
| 10,492,908 B2 * | 12/2019 | Hammer | A61F 2/2436 |
| 10,610,358 B2 * | 4/2020 | Vidlund | A61F 2/2418 |
| 10,952,844 B2 * | 3/2021 | Vidlund | A61F 2/2418 |
| 11,033,389 B2 * | 6/2021 | Solem | A61F 2/2427 |
| 11,039,921 B2 * | 6/2021 | Tegels | A61F 2/2418 |
| 11,096,782 B2 * | 8/2021 | Christianson | A61F 2/2418 |
| 11,179,236 B2 * | 11/2021 | Schankereli | A61F 2/2418 |
| 11,648,108 B2 * | 5/2023 | Liu | A61F 2/2418 623/2.17 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2004/0225354 A1 * | 11/2004 | Allen | A61F 2/2412 623/2.11 |
| 2005/0075727 A1 * | 4/2005 | Wheatley | A61F 2/2457 623/902 |
| 2005/0096726 A1 | 5/2005 | Sequin et al. | |
| 2005/0137695 A1 * | 6/2005 | Salahieh | A61F 2/2439 623/2.11 |
| 2005/0137697 A1 | 6/2005 | Salahieh et al. | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 * | 4/2006 | Huber | A61F 2/2412 623/2.14 |
| 2006/0106415 A1 | 5/2006 | Gabbay | |
| 2006/0122692 A1 | 6/2006 | Gilad et al. | |
| 2006/0142848 A1 | 6/2006 | Gabbay | |
| 2006/0149360 A1 | 7/2006 | Schwammenthal et al. | |
| 2006/0167468 A1 | 7/2006 | Gabbay | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0073391 A1 | 3/2007 | Bourang et al. | |
| 2007/0088431 A1 | 4/2007 | Bourang et al. | |

(56) References Cited

U.S. PATENT DOCUMENTS

| | | |
|---|---|---|
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0270943 A1* | 11/2007 | Solem .............. A61F 2/2466 606/151 |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1* | 10/2008 | Thambar ............ A61F 2/2436 623/2.11 |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1* | 8/2010 | Chau ................. A61F 2/2457 623/2.12 |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0224678 A1 | 9/2011 | Gabbay |
| 2012/0303116 A1 | 11/2012 | Gorman, III et al. |
| 2013/0079873 A1* | 3/2013 | Migliazza .......... A61F 2/2412 623/2.17 |
| 2013/0172978 A1 | 7/2013 | Vidlund et al. |
| 2013/0184811 A1* | 7/2013 | Rowe ................ A61F 2/2418 623/2.11 |
| 2014/0296969 A1* | 10/2014 | Tegels .............. A61F 2/2412 623/2.11 |
| 2014/0296975 A1* | 10/2014 | Tegels ................. A61F 2/07 623/2.18 |
| 2014/0358224 A1* | 12/2014 | Tegels .............. A61L 27/54 623/2.14 |
| 2016/0235525 A1 | 8/2016 | Rothstein et al. |
| 2017/0128209 A1 | 5/2017 | Morriss et al. |
| 2017/0312078 A1* | 11/2017 | Krivoruchko ....... A61F 2/2418 |
| 2017/0319333 A1* | 11/2017 | Tegels .............. A61B 17/0401 |
| 2018/0014932 A1* | 1/2018 | Hammer ............ A61F 2/2418 |
| 2019/0183642 A1* | 6/2019 | Tegels .................. A61F 2/2439 |
| 2019/0269839 A1* | 9/2019 | Wilson .............. A61M 60/148 |
| 2021/0030537 A1* | 2/2021 | Tegels .................. A61F 2/2409 |

FOREIGN PATENT DOCUMENTS

| | | | |
|---|---|---|---|
| DE | 102005003632 A1 | 8/2006 | |
| DE | 202008009610 U1 | 12/2008 | |
| EP | 0850607 A1 | 7/1998 | |
| EP | 1000590 A1 | 5/2000 | |
| EP | 1129744 A1 | 9/2001 | |
| EP | 1157673 A2 | 11/2001 | |
| EP | 1360942 A1 | 11/2003 | |
| EP | 1584306 A1 | 10/2005 | |
| EP | 1598031 A2 | 11/2005 | |
| EP | 1926455 A2 | 6/2008 | |
| FR | 2850008 A1 | 7/2004 | |
| FR | 2847800 B1 | 10/2005 | |
| WO | 9117720 A1 | 11/1991 | |
| WO | 9716133 A1 | 5/1997 | |
| WO | 9832412 A2 | 7/1998 | |
| WO | 9913801 A1 | 3/1999 | |
| WO | 2001028459 A1 | 4/2001 | |
| WO | 2001049213 A2 | 7/2001 | |
| WO | 0154625 A1 | 8/2001 | |
| WO | 0156500 A2 | 8/2001 | |
| WO | 0176510 A2 | 10/2001 | |
| WO | 0236048 A1 | 5/2002 | |
| WO | 0247575 A2 | 6/2002 | |
| WO | 02067782 A2 | 9/2002 | |
| WO | 03047468 A1 | 6/2003 | |
| WO | 2005070343 A1 | 8/2005 | |
| WO | 06073626 A2 | 7/2006 | |
| WO | 2007071436 A2 | 6/2007 | |
| WO | 08070797 A2 | 6/2008 | |
| WO | 2010008548 A2 | 1/2010 | |
| WO | 2010008549 A1 | 1/2010 | |
| WO | 10051025 A1 | 5/2010 | |
| WO | 10087975 A1 | 8/2010 | |
| WO | 2010096176 A1 | 8/2010 | |
| WO | 2010098857 A1 | 9/2010 | |
| WO | WO-2013028387 A2 * | 2/2013 | ........... A61F 2/2409 |
| WO | WO-2018218121 A1 * | 11/2018 | ........... A61F 2/2421 |
| WO | WO-2019057185 A1 * | 3/2019 | ............... A61F 2/24 |

OTHER PUBLICATIONS

"Direct-Access Valve Replacement", Christoph H. Huber, et al., Journal of the American College of Cardiology, vol. 46, No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Mar. 23, 2006).

"Percutaneous Aortic Valve Implantation Retrograde From the Femoral Artery", John G. Webb et al., Circulation, 2006; 113:842-850 (Feb. 6, 2006).

"Percutaneous Aortic Valve Replacement: Resection Before Implantation", Quaden, Rene et al., European J. of Cardio-Thoracic Surgery, vol. 27, No. 5, May 2005, pp. 836-840.

"Transapical aortic valve implantation: an animal feasibility study"; Todd M. Dewey et al., The annals of thoracic surgery 2006; 82: 110-6 (Feb. 13, 2006).

"Transapical Transcatheter Aortic Valve Implantation in Humans", Samuel V. Lichtenstein et al., Circulation. 2006; 114: 591-596 (Jul. 31, 2006).

"Transluminal Aortic Valve Placement. A Feasability Study with a Newly Designed Collapsible Aortic Valve", Moazami et al., ASAIO Journal, vol. 42, No. 5, 1996, pp. M381-M385.

"Transluminal Catheter Implanted Prosthetic Heart Valves", Andersen, H. R., International Journal of Angiology, vol. 7, No. 2, Mar. 1998, pp. 102-106.

"Transluminal Implantation of Artificial Heart Valves", Andersen, H. R., et al., European Heart Journal, vol. 13, No. 5, May 1992, pp. 704-708.

Closed Heart Surgery: Back to the Future, Samuel V. Lichtenstein, The Journal of Thoracic and Cardiovascular Surgery, vol. 131, No. 5, May 2006, pp. 941-943.

(56) References Cited

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Ruiz, Carlos, Overview of PRE-CE Mark Transcatheter Aortic Valve Technologies, Euro PCR—dated May 25, 2010?
Transapical Approach for Sutureless Stent-Fixed Aortic Valve Implantation: Experimental Results, Th. Walther et al., European Journal of Cardio-Thoracic Surgery, vol. 29, No. 5, May 2006, pp. 703-708.
Transcatheter Valve Repair, Hijazi et al., CRC Press, Jan. 2006, pp. 165-186.
U.S. Appl. No. 29/375,243, filed Sep. 20, 2010—Braido, et al., U.S. Appl. No. 29/375,243, filed Sep. 20, 2010, titled "Surgical Stent Assembly".
International Search Report for PCT/US2021/041243 mailed Oct. 28, 2021 (3 pages).

\* cited by examiner

TETHER ATTACHMENT FOR MITRAL VALVE

CROSS-REFERENCE TO RELATED APPLICATIONS

This application claims the benefit of the filing date of U.S. Provisional Patent Application No. 63/052,160 filed on Jul. 15, 2020 the disclosure of which is hereby incorporated herein by reference.

BACKGROUND OF THE DISCLOSURE

The present disclosure relates to collapsible and expandable prosthetic heart valves, and more particularly, to apparatus and methods for stabilizing a collapsible and expandable prosthetic heart valve within a native annulus of a patient.

Prosthetic heart valves that are collapsible to a relatively small circumferential size can be delivered into a patient less invasively than valves that are not collapsible. For example, a collapsible and expandable valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible and expandable prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed to reduce its circumferential size.

When a collapsed prosthetic valve has reached the desired implant site in the patient (e.g., at or near the native annulus of the patient's heart valve that is to be repaired by the prosthetic valve), the prosthetic valve can be deployed or released from the delivery apparatus and expanded to its full operating size. For balloon-expandable valves, this generally involves releasing the entire valve, assuring its proper location, and then expanding a balloon positioned within the valve stent. For self-expanding valves, on the other hand, the stent automatically expands as the stent is withdrawn from the delivery apparatus.

The clinical success of collapsible and expandable heart valves is dependent, in part, on the anchoring of the valve within the native valve annulus. Self-expanding valves typically rely on the radial force exerted by expanding the stent against the native valve annulus to anchor the prosthetic heart valve. However, if the radial force is too high, the heart tissue may be damaged. If, instead, the radial force is too low, the heart valve may move from its deployed position and/or migrate from the native valve annulus, for example, into the left ventricle.

Movement of the prosthetic heart valve may result in the leakage of blood between the prosthetic heart valve and the native valve annulus. This phenomenon is commonly referred to as paravalvular leakage. In mitral valves, paravalvular leakage enables blood to flow from the left ventricle back into the left atrium during ventricular systole, resulting in reduced cardiac efficiency and strain on the heart muscle.

Anchoring prosthetic heart valves within the native valve annulus of a patient, especially within the native mitral valve annulus, can be difficult. For instance, the native mitral valve annulus has reduced calcification or plaque compared to the native aortic valve annulus, for example, which can make for a less stable surface to anchor the prosthetic heart valve. For this reason, collapsible and expandable prosthetic mitral valves often include additional anchoring features such as a tether. The tether is commonly secured to an apical pad placed at the apex of the heart to anchor the prosthetic heart valve in position within the native valve annulus of the patient.

Despite the improvements that have been made to anchoring collapsible and expandable prosthetic heart valves, shortcomings remain. For example, to accommodate the tether, the prosthetic heart valve often extends at least partially into the ventricle, which can impede blood flow to the Left Ventricular Outflow Tract (LVOT).

BRIEF SUMMARY OF THE DISCLOSURE

In accordance with a first aspect of the present disclosure, a collapsible and expandable prosthetic heart valve having a low-profile is provided. Among other advantages, the prosthetic heart valve is designed to be securely anchored within the native mitral valve annulus without projecting into the ventricle. As a result, the prosthetic heart valve disclosed herein minimizes the obstruction of blood flow to the LVOT.

One embodiment of the prosthetic heart valve includes a prosthetic heart valve having an expandable stent with an inflow end and an outflow end, a valve assembly disposed within the stent including a cuff and a plurality of leaflets, a tether connector positioned between the inflow end and the valve assembly and a tether secured to the tether connector.

A method of implanting a prosthetic heart valve within a native heart valve annulus is provided herein and includes delivering a delivery device to a target site adjacent to a native valve annulus while the delivery device holds a prosthetic heart valve including a stent, a valve assembly disposed within the stent and a tether attached to the stent; deploying the prosthetic heart valve from the delivery device within the native valve annulus; creating a passage through the wall of the heart; extending the tether through the valve assembly and through the passage to a location outside the heart; attaching an apical pad to the tether; tensioning the tether; and securing the apical pad against an external surface of the heart.

BRIEF DESCRIPTION OF THE DRAWINGS

Various embodiments of the present disclosure are described herein with reference to the drawings, wherein.

DETAILED DESCRIPTION

Blood flows through the mitral valve from the left atrium to the left ventricle. As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. Also as used herein, the terms "substantially," "generally," "approximately," and "about" are intended to mean that slight deviations from absolute are included within the scope of the term so modified.

Figure 1:
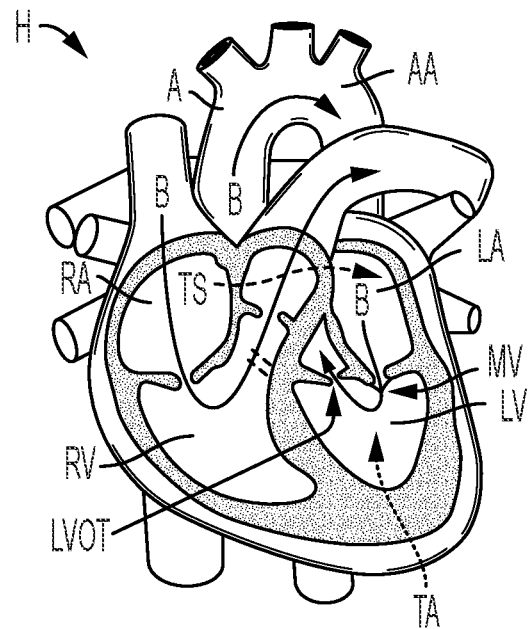
FIG. 1 is a highly schematic cutaway view of the human heart, showing two approaches for delivering a prosthetic mitral valve to an implantation location.

FIG. 1 is a schematic cutaway representation of a human heart H. The human heart includes two atria and two ventricles: right atrium RA and left atrium LA, and right ventricle RV and left ventricle LV. Heart H further includes aorta A, aortic arch AA and left ventricular outflow tract LVOT. Disposed between the left atrium and the left ventricle is mitral valve MV. The mitral valve, also known as the bicuspid valve or left atrioventricular valve, is a dual-flap that opens as a result of increased pressure in left atrium LA as it fills with blood. As atrial pressure increases above that in left ventricle LV, mitral valve MV opens and blood flows into the left ventricle. When left ventricle LV contracts during ventricular systole, blood is pushed from the left ventricle, through left ventricular outflow tract LVOT and into aorta A. Blood flows through heart H in the direction shown by arrows "B".

A dashed arrow, labeled "TA", indicates a transapical approach of implanting a prosthetic heart valve, in this case to replace the mitral valve. In the transapical approach, a small incision is made between the ribs of the patient and into the apex of left ventricle LV to deliver the prosthetic heart valve to the target site. A second dashed arrow, labeled "TS", indicates a transseptal approach of implanting a prosthetic heart valve in which the delivery device is inserted into the femoral vein, passed through the iliac vein and the superior vena cava into the right atrium RA, and then through the atrial septum into the left atrium LA for deployment of the valve. Other approaches for implanting a prosthetic heart valve are also possible and may be used to implant the collapsible prosthetic heart valve described in the present disclosure.

Figure 2:
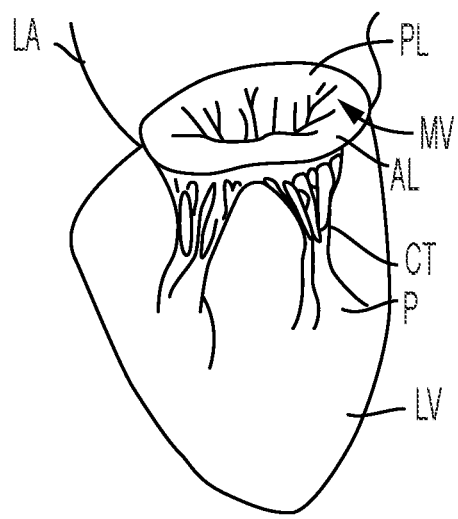
FIG. 2 is a highly schematic representation of a native mitral valve and associated cardiac structures.

FIG. 2 is a more detailed schematic representation of native mitral valve MV and its associated structures. As previously noted, mitral valve MV includes two flaps or leaflets, posterior leaflet PL and anterior leaflet AL, disposed between left atrium LA and left ventricle LV. Cord-like tendons, known as chordae-tendineae CT, connect the two leaflets to the medial and lateral papillary muscles P. During atrial systole, blood flows from higher pressure in left atrium LA to lower pressure in left ventricle LV. When left ventricle LV contracts during ventricular systole, the increased blood pressure in the chamber pushes the posterior and anterior leaflets to close, preventing the backflow of blood into left atrium LA. Since the blood pressure in left atrium LA is much lower than that in left ventricle LV, the leaflets attempt to evert to low pressure regions. Chordae tendineae CT prevent the eversion by becoming tense, thus pulling on the leaflets and holding them in the closed position.

Figure 3:
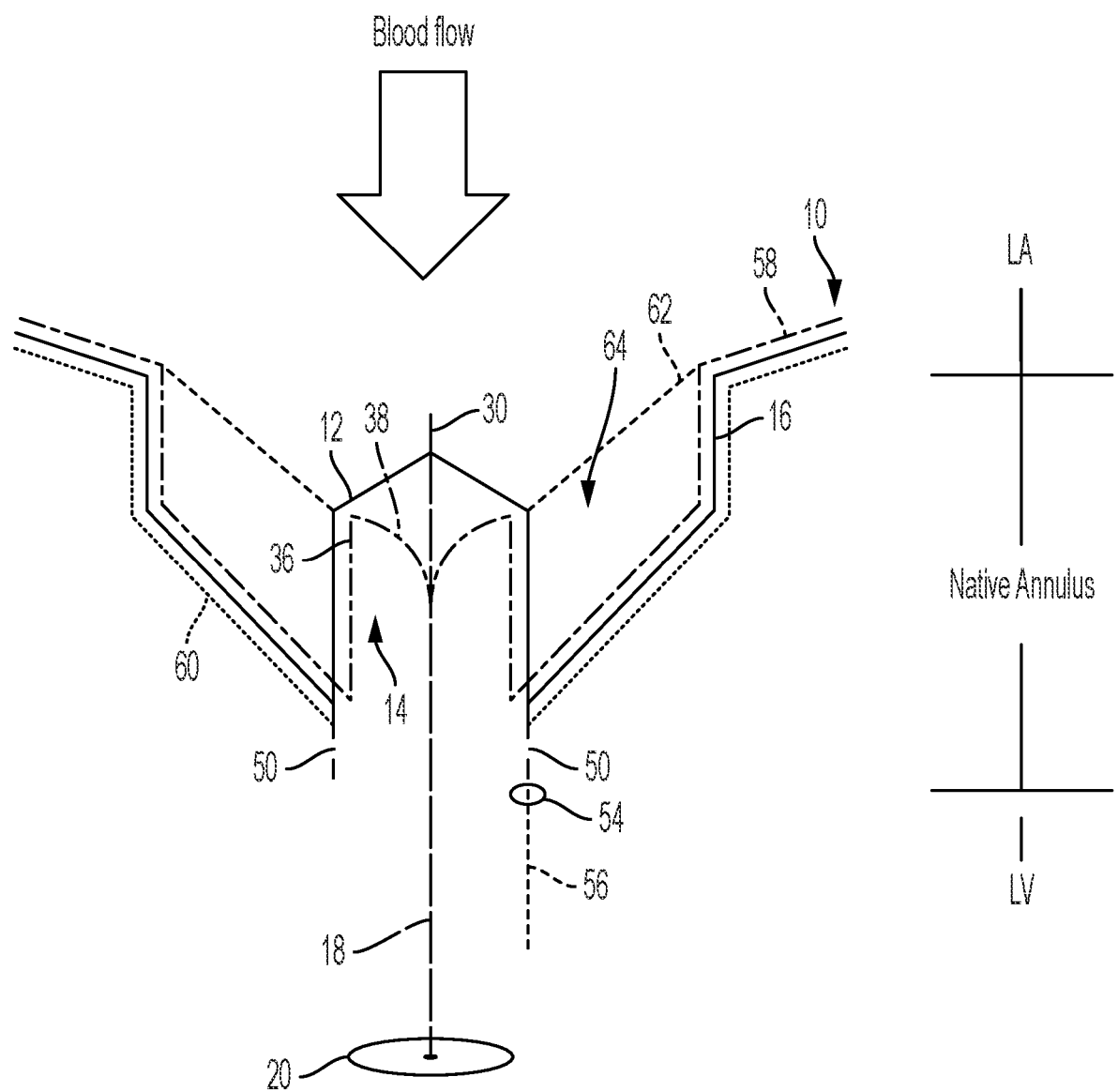
FIG. 3 is a highly schematic longitudinal cross-section of a prosthetic mitral valve according to an embodiment of the present disclosure.

FIG. 3 is highly schematic longitudinal cross-section of a collapsible and expandable prosthetic heart valve 10 according to an embodiment of the present disclosure. For balloon-expandable variants, prosthetic heart valve 10 may be expandable, but not collapsible, or not readily collapsible, once expanded. When used to replace native mitral valve MV (shown in FIG. 1), prosthetic valve 10 may have a low profile so as minimize any interference with the heart's electrical conduction system pathways, atrial function or blood flow to the left ventricular outflow tract LVOT (shown in FIG. 1).

Prosthetic heart valve 10 includes an inner stent 12 securing a valve assembly 14, an outer stent 16 attached to and disposed around the inner stent, and a tether 18 configured to be secured to an apical pad 20. Both the inner stent 12 and the outer stent 16 may be formed from biocompatible materials that are capable of self-expansion, for example, shape-memory alloys such as nitinol. Alternatively, inner stent 12 and/or outer stent 16 may be balloon expandable or expandable by another force exerted radially outward on the stent. When expanded, outer stent 16 may exert an outwardly directed radial force against the native valve annulus that assists in anchoring inner stent 12 and valve assembly 14 within the native annulus.

Figure 4:
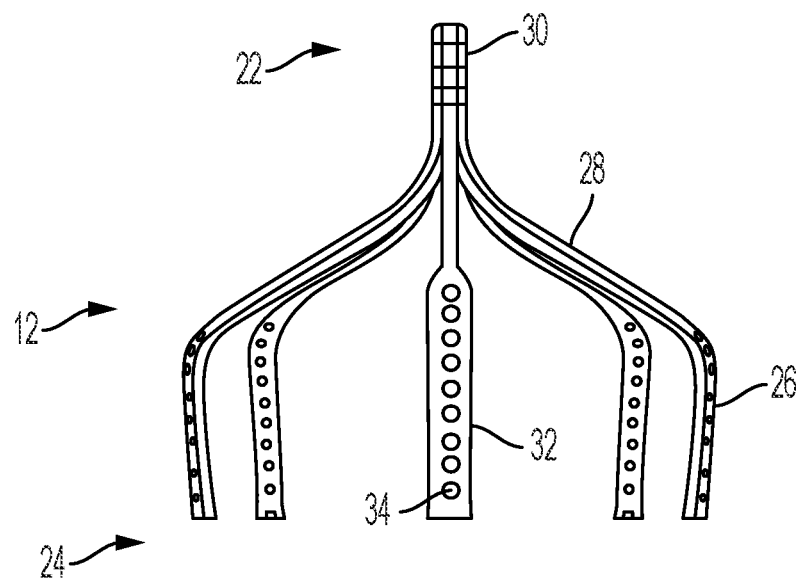
FIG. 4 is a side elevational view of an inner stent of the prosthetic mitral valve of FIG. 3.

Referring to FIG. 4, inner stent 12 extends along a longitudinal axis between an inflow end 22 and an outflow end 24. In one example, inner stent 12 is formed by laser cutting a predetermined pattern into a metallic tube, such as a nitinol tube, to form three portions: a body portion 26, a strut portion 28 and a tether connector 30 that secures tether 18 (shown in FIG. 3). As shown in FIG. 4, body portion 26 is positioned at the outflow end 24 of inner stent 12, tether connector 30 is positioned at the inflow end 22 of the inner stent and strut portion 28 extends between the body portion and the tether connector. Strut portion 28 may include, for example, six struts that extend radially inward from body portion 26 to tether connector 30. When inner stent 12 is expanded, tether connector 30 and, in turn, tether 18 are positioned along the longitudinal axis of the inner stent to centrally anchor prosthetic heart valve 10. Body portion 26 may include six longitudinal posts 32 having one or more bores 34 for securing valve assembly 14 to the inner stent 12 by one or more sutures.

With additional reference to FIG. 3, valve assembly 14 may be secured to inner stent 12 by suturing the valve assembly to longitudinal posts 32. Valve assembly 14 includes a cuff 36 and a plurality of leaflets 38 that open and close collectively to function as a one-way valve. Cuff 36 and leaflets 38 may be wholly or partly formed of any suitable biological material, such as bovine or porcine pericardium, or biocompatible polymer, such as polytetrafluorethylene (PTFE), urethanes and the like. The bores 34 of longitudinal posts 32 facilitate the suturing of the leaflet commissure to the body portion 26 of inner stent 12.

Figure 5:
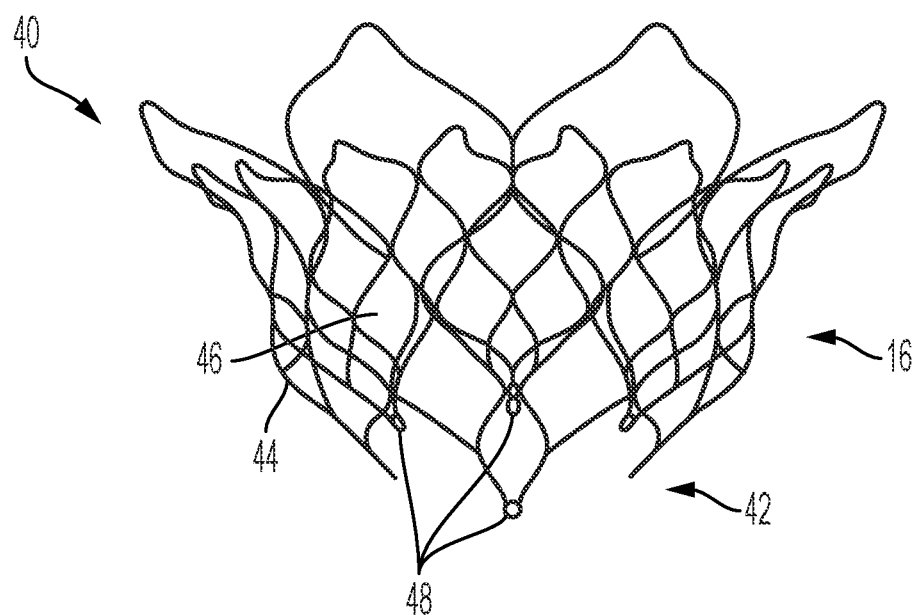
FIG. 5 is a side elevational view of an outer stent of the prosthetic mitral valve of FIG. 3.

Turning now to FIG. 5, outer stent 16 extends between an atrial end 40 and a ventricular end 42 along the same longitudinal axis as inner stent 12. Outer stent 16 may include a plurality of struts 44 that form cells 46 extending about the outer stent in one or more annular rows. In one example, outer stent 16 is formed by laser cutting a predetermined pattern into a metallic tube, such as a self-expanding nitinol tube. Cells 46 may be substantially the same size around the perimeter of stent 16 and along the length of the stent. Alternatively, cells 46 near the atrial end 40 of outer stent 16 may be larger than the cells near the ventricular end 42. A plurality of attachment features 48 may lie at the intersections of the struts 44 that form the cells 46 at the ventricular end 42 of outer stent 16. Attachment features 48 may include an eyelet that facilitates the suturing of outer stent 16 to the longitudinal posts 32 of inner stent 12, thereby securing the inner and outer stents together. In one example, each attachment feature 48 may be sutured to a single bore 34 of longitudinal post 32, proximate to the outflow end 24 of inner stent 12. With further reference to FIG. 3, a pair of diametrically opposed retaining loops 50 may be provided on the ventricular end 42 of outer stent 16. Each retaining loop 50 is designed to receive a looped suture 52 (shown in FIGS. 7A and 7B) to cinch the ventricular end 42 of outer stent 16 toward the longitudinal axis if repositioning or complete retrieval of prosthetic heart valve 10 is required after the prosthetic heart valve has been fully deployed.

When outer stent 16 is expanded, the struts 44 forming the cells 46 in the annular row of cells adjacent the atrial end 40 of the outer stent may bend about the midsections of the cells (e.g., in a direction generally orthogonal to the longitudinal axis) such that the upper apexes of the cells extend radially outward relative to the midsections of the cells and collectively form an atrial flange. The flange is designed to protrude into the left atrium LA and engage an upper surface of the native mitral valve annulus when prosthetic valve 10 is disposed within the native mitral valve MV, thereby preventing the mitral valve from migrating into left ventricle LV. Prosthetic heart valve 10 is anchored within the native mitral valve annulus by the radial force exerted by outer stent 16 against the native annulus, the flange engaging the atrial surface of the native valve annulus and the tether anchored to the ventricular wall of the heart. As is schematically shown in FIG. 3, the flange is the only portion of prosthetic heart valve 10 that is designed to extend out from the native mitral valve annulus. Put another way, inner stent 12 and outer stent 16 are designed with a low-profile so as to not extend into left ventricle LV. In this manner, prosthetic heart valve 10 does not interfere with blood flow to the left ventricular outflow tract LVOT. The low-profile design is possible, in part, because tether connector 30 is positioned upstream of valve assembly 14, for example, adjacent the atrial end 40 of outer stent 16. When prosthetic heart valve 10 is implanted within the native mitral valve annulus and tether 18 is anchored to the apex of the heart, the tether extends through valve assembly 14 from tether connector 30 to apical pad 20. During ventricular systole, leaflets 38 close around tether 18.

Due to the low-profile of prosthetic heart valve 10, Systolic Anterior Motion (SAM) prevention features may optionally be provided, for example, on outer stent 16. SAM (e.g., the displacement of the free edge of native anterior leaflet AL toward left ventricular outflow tract LVOT) can result in severe left ventricular outflow tract LVOT obstruction and/or mitral regurgitation. To prevent the occurrence of SAM, or at least significantly reduce its likelihood, a ring 54 may be positioned on an anterior side of outer stent 16. A cord 56 attached at one end to ring 54 may be inserted through native anterior leaflet AL (shown in FIGS. 1 and 2) to secure the native anterior leaflet to prosthetic heart valve 10. In one embodiment, ring 54 may extend from one of attachment features 48 positioned on an anterior side of outer stent 16. Ring 54 may alternatively lie at an intersection of two struts 44 that form a cell 46 at the ventricular end 42 and anterior side of outer stent 16.

In a preferred embodiment, prosthetic heart valve 10 may include an inner skirt 58, an outer skirt 60 and a cover 62. Outer skirt 60 may be disposed about the abluminal surface of outer stent 16 and may be formed of a polyester fabric that promotes tissue ingrowth. Inner skirt 58 may be disposed about the luminal surface of outer stent 16 and may be formed of any suitable biological material, such as bovine or porcine pericardium, or any suitable biocompatible polymer, such as PTFE, urethanes or similar materials. When prosthetic heart valve 10 is secured within the native mitral valve annulus, inner skirt 58 acts in combination with outer skirt 60 to prevent mitral regurgitation, or the flow of blood between the prosthetic heart valve 10 and the native mitral valve annulus. In one embodiment, inner skirt 58 and outer skirt 60 extend only between the atrial end 40 of outer stent 16 and attachment features 48 to facilitate the suturing of the outer stent to inner stent 12. Cover 62 may be attached from the atrial end 40 of outer stent 16 to the junction of body portion 26 and strut portion 28 of inner stent 12 such that the cover extends across a gap defined between the inner stent and the outer stent, forming a pocket 64 underneath the cover and between the inner and outer stents. Cover 62 may be formed from a porous polyester mesh material. The pores of the mesh material are preferably of a size that allows antegrade blood to flow into pocket 64, but prevents coagulated blood, or thrombosis, from leaving the pocket.

Prosthetic heart valve 10 may be used to repair a malfunctioning native heart valve, such as a native mitral valve, or a previously implanted and malfunctioning prosthetic heart valve. Although prosthetic heart valve 10 is described herein as repairing a native mitral valve, it will be appreciated that the prosthetic heart valve may be used to repair other cardiac valves such as the aortic valve. Once prosthetic heart valve 10 has been properly positioned within the native mitral valve annulus of the patient, it works as a one-way valve, allowing blood to flow into left ventricle LV, and preventing blood from returning to left atrium LA.

Figure 6:
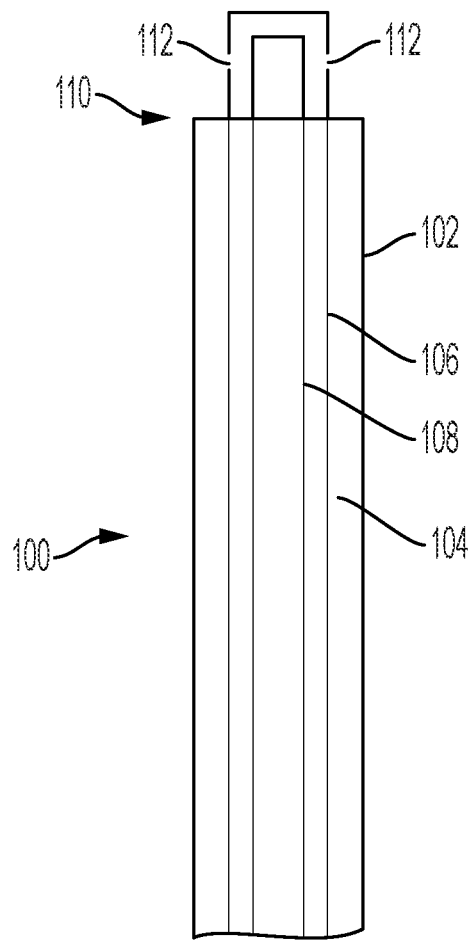
FIG. 6 is a highly schematic partial side view of a delivery catheter for deploying the prosthetic mitral valve of FIG. 3.

FIG. 6 is a partial, schematic illustration of a delivery device 100 for implanting the prosthetic heart valve, and if necessary, repositioning or removing it from the native mitral annulus of the patient after the prosthetic heart valve has been deployed from the delivery device. While delivery device 100 is described herein as delivering prosthetic heart valve 10 to the native mitral valve annulus using a transapical approach, it will be appreciated that the prosthetic heart valve may alternatively be delivered using a transseptal or another approach.

Delivery device 100 includes a handle (not shown) connected to a delivery tube 102 having a lumen 104 therethrough, an outer dilator 106 disposed within the lumen of the delivery tube and an inner dilator 108 disposed within the lumen of the outer dilator. The handle may include one or more actuators, such as rotatable knobs, linear slides, pull handles, levers, or buttons, for controlling the operation of delivery device 100. Delivery tube 102 extends from a leading end 110 to a trailing end (not shown) at which the delivery tube is operably connected to the handle. Delivery device 100 may be any tube-like delivery device, such as a catheter, a trocar, a laparoscopic instrument, or the like, configured to house prosthetic heart valve 10 as the delivery device is advanced toward the native mitral valve annulus.

In one embodiment, delivery tube 102 may be mounted on a carriage (not shown) that is slidably mounted within the handle. The carriage is thus configured to retract delivery tube 102 to deploy prosthetic heart valve 10 from the leading end 110 of the delivery tube. By way of example, the carriage may be coupled to a first actuator, which may be a rotatable knob that precisely controls movement of delivery tube 102, and/or a linearly translatable actuator such as a slide that quickly translates the carriage and, in turn, the delivery tube.

Figure 7A:
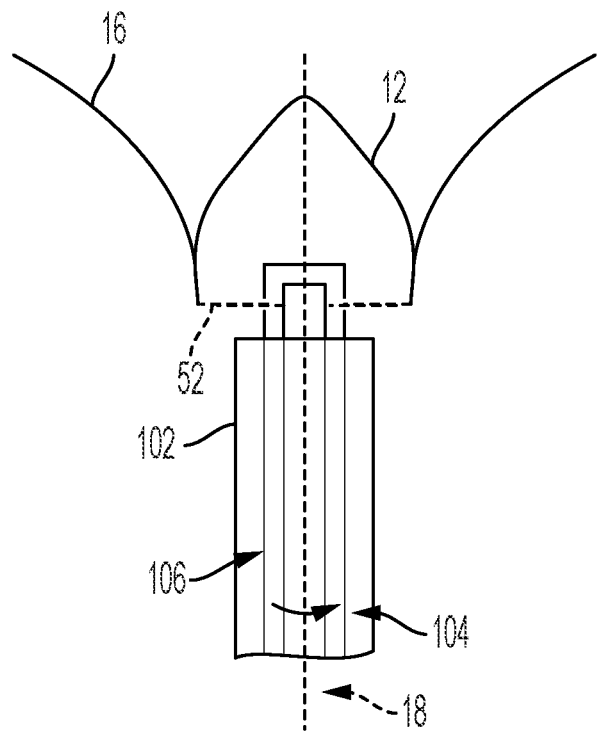
FIG. 7A is a highly schematic side elevational view illustrating deployment of the prosthetic mitral valve of FIG. 3 within the native mitral valve annulus.
Figure 7B:
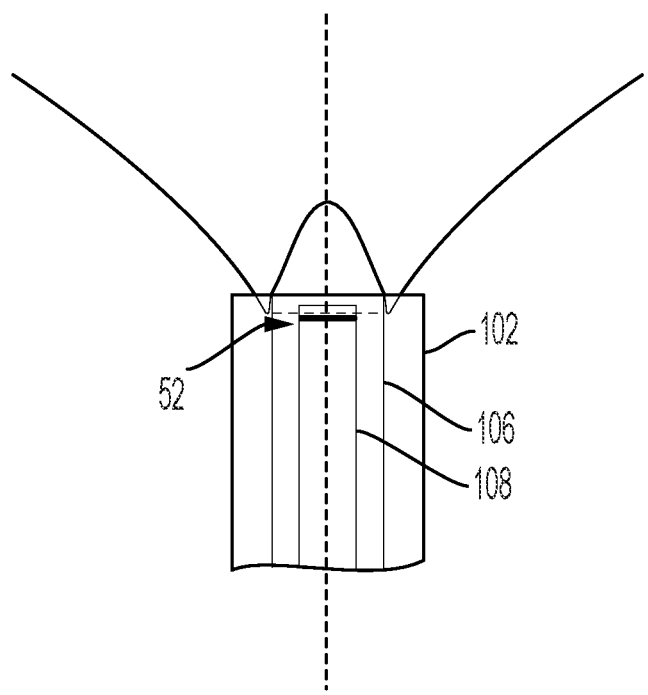
FIG. 7B is a highly schematic side elevational view illustrating retrieval of the prosthetic mitral valve of FIG. 3 from the native mitral valve annulus.

Inner dilator 108 may be rotatably disposed within the lumen of outer dilator 106. Rotation of inner dilator 108 may be controlled by a second actuator disposed on the handle. The second actuator may, for example, be a manually operated rotatable knob or a button that activates a motorized rotation mechanism. A pair of suture receiving clips or another suture attachment mechanism (not shown) may be provided adjacent the leading end of inner dilator 108. Outer dilator 106 may have a pair of diametrically opposed holes 112 at its leading end and proximate the suture clips of inner dilator 108. In this manner, sutures 52, attached to the retaining loops 50 of prosthetic heart valve 10, may be threaded through holes 112 of outer dilator 106 and secured to the suture clips of inner dilator 108 as shown in FIGS. 7A and 7B. Both inner dilator 108 and outer dilator 106 may have open leading ends, with the inner dilator also having a lumen extending from its leading end to its trailing end for receiving the tether 18 of prosthetic heart valve 10.

The use of delivery device 100 to deliver and, if necessary, reposition or retrieve prosthetic heart valve 10, will now be described with reference to FIGS. 7A and 7B. With delivery tube 102 in a retracted condition to expose the dilators, a physician may initially couple prosthetic heart valve 10 to delivery device 100 by inserting suture 52 through and around the retaining loops 50 of outer stent 16, through the holes 112 of outer dilator 106 and into engagement with the suture clips of inner dilator 108. Prosthetic heart valve 10 may then be collapsed and delivery tube 102 may be extended to load the heart valve within delivery device 100 such that the prosthetic heart valve is positioned between dilators 106, 108 and the leading end 110 of the delivery tube. Tether 18 may be fed from its connection to the prosthetic heart valve, through the open end and lumen of inner dilator 108 and out from the trailing end of the inner dilator such that the free end of the tether may be engaged with a tether retention mechanism, such as a tether pin, located on the handle of the delivery device. The amount of clearance between tether 18 and the inner wall of inner dilator 108 is such that the tether is not affected by the rotation of the inner dilator.

After an incision has been made between the ribs of the patient and into the apex of the heart, delivery device 100 may be percutaneously introduced into the patient using a transapical approach and delivered to an implant site adjacent the native mitral valve annulus. Once delivery device 100 has reached the target site, the first actuator may be actuated to retract delivery tube 102. Actuation of the first actuator will unsheathe prosthetic heart valve 10, allowing outer stent 16 to expand from the collapsed condition and engage the native valve annulus, while also allowing inner stent 12 to expand from the collapsed condition to the expanded condition within the outer stent. After the inner stent 12 and the outer stent 16 have been expanded, a physician may determine whether prosthetic heart valve 10 has restored proper blood flow through the native mitral valve. More particularly, the physician may determine: 1) whether valve assembly 14 is functioning properly; and 2) whether the prosthetic heart valve 10 has been properly seated within the native valve annulus to form a seal between the prosthetic heart valve and the native mitral valve annulus.

In the event that the physician determines that the valve assembly 14 is malfunctioning or that prosthetic heart valve 10 is positioned incorrectly within the native mitral annulus, the physician may recapture the prosthetic heart valve. To recapture prosthetic heart valve 10, the physician may actuate the second actuator which causes inner dilator 108 to rotate about its axis relative to outer dilator 106 and delivery tube 102. Rotation of inner dilator 108 results in sutures 52 wrapping about the inner dilator and forcing the ventricular end 42 of outer stent 16 to collapse toward the longitudinal axis to a diameter capable of being inserted into the leading end 110 of delivery tube 102, for example, a diameter of equal to or less than approximately 36 French. Collapsing the ventricular end 42 of outer stent 16 similarly collapses the outflow end 24 of inner stent 12. With the ventricular end 42 of outer stent 16 and the outflow end of inner stent 12 collapsed, tether 18 may be disengaged from the tether retention mechanism and retracted toward the trailing end of delivery device 100 to pull the outer stent, and with it inner stent 12, within delivery tube 102. If valve assembly 14 was working as intended, but prosthetic heart valve 10 was mispositioned within the native mitral valve annulus, the physician may only need to partially collapse the prosthetic heart valve within delivery tube 102 before repositioning the delivery tube with respect to the native mitral annulus and redeploying the prosthetic heart valve as previously described. Alternatively, if valve assembly 14 was malfunctioning, prosthetic heart valve 10 may be completely recaptured and removed from the patient. The physician may then repeat the procedure described above with a different prosthetic heart valve 10.

Once the physician has confirmed that prosthetic heart valve 10 has been properly positioned within the native annulus of the patient, sutures 52 may be cut or otherwise disengaged from inner dilator 108. Delivery device 100 may then be removed from the patient.

In some instances, the physician may find it desirable to secure the native anterior leaflet AL of native mitral valve MV to the outer stent 16 of prosthetic mitral valve 10 to prevent SAM. Using a clamp (not shown) and a needle (not shown), or another piercing tool, the physician may hold the anterior leaflet while piercing a hole through the leaflet. Cord 56 may then be inserted through the hole and tied to the native anterior leaflet to secure the native leaflet to prosthetic heart valve 10.

Once the prosthetic heart valve 10 has been properly positioned in the native valve annulus, the physician may pull tether 18 through the puncture at the apex of the heart so that the tether extends out from the left ventricle LV of the heart. Apical pad 20 may then be inserted through the incision between the ribs of the patient and placed against an external surface of the heart before tether 18 is tensioned and secured to the apical pad. With prosthetic heart valve 10 properly positioned and anchored within the native mitral valve annulus of a patient, the prosthetic heart valve may work as a one-way valve to restore proper function of the heart valve by allowing blood to flow in one direction (e.g., from the left atrium to the left ventricle) while preventing blood from flowing in the opposite direction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A prosthetic heart valve, comprising:
an expandable inner stent having an inflow end and an outflow end;
an expandable outer stent having an atrial end and a ventricular end, the outer stent being secured to and at least partially surrounding the inner stent;
a valve assembly disposed within the inner stent, the valve assembly including a cuff and a plurality of leaflets;

a tether connector positioned at the inflow end of the inner stent and also along a central longitudinal axis of the inner stent when the inner stent is in an expanded condition; and a tether having a first end and a second end remote from the first end, the first end of the tether being secured to the tether connector so that a length of the tether between the first end and the second end extends along the central longitudinal axis, wherein the plurality of leaflets are positioned relative to the tether such that, in an implanted condition of the prosthetic heart valve, the plurality of leaflets are configured to close around the tether during ventricular systole.

2. The prosthetic heart valve of claim 1, wherein the outflow end of the inner stent is disposed completely between the atrial end and the ventricular end of the outer stent when the inner stent is in the expanded condition and when the outer stent is in an expanded condition.

3. The prosthetic heart valve of claim 1, wherein the ventricular end of the outer stent in an expanded condition has a first diameter and the atrial end of the outer stent in the expanded condition has a second diameter larger than the first diameter.

4. The prosthetic heart valve of claim 1, wherein the inflow end of the inner stent in the expanded condition has a first diameter and the outflow end of the inner stent in the expanded condition has a second diameter larger than the first diameter.

5. The prosthetic heart valve of claim 1, further comprising:

a tissue skirt disposed about a luminal surface of the outer stent;

a fabric skirt disposed about an abluminal surface of the outer stent; and a mesh cover attached from the atrial end of the outer stent to a portion of the inner stent.

6. The prosthetic heart valve of claim 1, wherein the ventricular end of the outer stent includes a pair of retaining loops.

7. The prosthetic heart valve of claim 6, further comprising a suture coupled to each of the retaining loops for crimping the ventricular end of the outer stent.

8. The prosthetic heart valve of claim 1, further comprising a ring disposed at the ventricular end and on an anterior side of the outer stent.

9. The prosthetic heart valve of claim 8, further comprising a cord attached to the ring and configured to be secured the native anterior leaflet.

10. The prosthetic heart valve of claim 1, wherein the tether connector is positioned adjacent the atrial end of the outer stent.

11. The prosthetic heart valve of claim 1, further comprising an apical pad for holding the tether in a tensioned condition.

* * * * *